(12) United States Patent
Lee et al.

(10) Patent No.: US 11,568,962 B2
(45) Date of Patent: Jan. 31, 2023

(54) METHOD FOR PREDICTING DRUG-DRUG OR DRUG-FOOD INTERACTION BY USING STRUCTURAL INFORMATION OF DRUG

(71) Applicant: KOREA ADVANCED INSTITUTE OF SCIENCE AND TECHNOLOGY, Daejeon (KR)

(72) Inventors: Sang Yup Lee, Daejeon (KR); Jae Yong Ryu, Daejeon (KR); Hyun Uk Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 327 days.

(21) Appl. No.: 16/766,690

(22) PCT Filed: Nov. 20, 2018

(86) PCT No.: PCT/KR2018/013936
§ 371 (c)(1),
(2) Date: May 24, 2020

(87) PCT Pub. No.: WO2019/107804
PCT Pub. Date: Jun. 6, 2019

(65) Prior Publication Data
US 2021/0375400 A1    Dec. 2, 2021

(30) Foreign Application Priority Data

Dec. 1, 2017    (KR) .................. 10-2017-0164115

(51) Int. Cl.
*G16C 20/30*    (2019.01)
*G16H 70/40*    (2018.01)
(Continued)

(52) U.S. Cl.
CPC ............... *G16C 20/30* (2019.02); *G06N 3/08* (2013.01); *G16C 20/70* (2019.02); *G16H 70/40* (2018.01); *A61B 5/4848* (2013.01)

(58) Field of Classification Search
CPC ........ G16C 20/30; G16C 20/70; G16C 20/10; G06N 3/08; G06N 3/0454; G16H 70/40; G16H 50/20; G16H 50/70; A61B 5/4848
See application file for complete search history.

(56) References Cited

U.S. PATENT DOCUMENTS

2003/0229456 A1* 12/2003 Beger .................... G01N 33/48
702/27
2015/0324693 A1   11/2015 Hu et al.
(Continued)

FOREIGN PATENT DOCUMENTS

JP    2017084350 A    5/2017
JP    2017084340 A    7/2020
(Continued)

OTHER PUBLICATIONS

Gomez-Bombarelli, R., et al., "Automatic Chemical Design Using a Data-Driven Continuous Representatioin of Molecules", "ACS Cent. Sei ", 2018, pp. 268-276, vol. 4.
(Continued)

*Primary Examiner* — Reginald R Reyes
(74) *Attorney, Agent, or Firm* — Hultquist, PLLC; Steven J. Hultquist

(57) ABSTRACT

The present invention relates to a method for predicting a drug-drug interaction and a drug-food interaction by using structural information of a drug and, more particularly, to a method for predicting the mechanism of action and activity of a drug interaction through interaction prediction results expressed by a standardized sentence. When using a method for predicting a drug interaction according to the present invention, a drug interaction can be predicted quickly and
(Continued)

accurately, and in particular, activity information of an unknown compound can also be predicted by expressing a prediction result by means of a sentence, and thus the method is very useful for developing a drug exhibiting desired activity without causing adverse effects.

5 Claims, 11 Drawing Sheets

(51) Int. Cl.
*G16C 20/70* (2019.01)
*G06N 3/08* (2006.01)
*A61B 5/00* (2006.01)

(56) References Cited

U.S. PATENT DOCUMENTS

2016/0303553 A1* 10/2016 Chorghade ............ C07F 15/025
2017/0116390 A1  4/2017 Fokoue-Nkoutche

FOREIGN PATENT DOCUMENTS

| KR | 20160149623 A | 12/2016 |
| KR | 20160149624 A | 12/2016 |
| KR | 20170092815 A | 8/2017 |

OTHER PUBLICATIONS

Jaeger, S., et al., "Mol2vec: Unsupervised Machine Learning Approach with Chemical Intuition", "J. Chem. Inf. Model.", 2018, pp. 27-35, vol. 58.

Shah, R., "Pharmacologenetic Aspects of Drug-Induced Torsade de Pointes: Potential Tool for Improving Clinical Drug Development and Prescribing", "Drug Safety", 2004, pp. 145-172, vol. 27, No. 3.

Tatonetti, N., et al., "A Novel Signal Detection Algorithm for Identifying Hidden Drug-Drug Interactions in Adverse Event Reports", "J. Am. Med.Infor. Assoc.", 2012, pp. 79-85, vol. 19.

Fokoue, A., et al., "Predicting Drug-Drug Interactions Through Large-Scale Similarity-Based Link Prediction", Conference Paper, 2016, pp. 774-789; DOI:10.007/978-3-319-34129-3_47, Publisher: Springer International Publishing Switzerland.

Jensen, K., et al., "Developing a Molecular Roadmap of Drug-Food Interactions", PLOS Computational Biology, 2015, Page(s) DOI: 10.1371/journal.pcbi.1004048.

Kwon, S., et al., "DeepCCI: End-to-end Deep Learning for Chemical-Chemical Interaction Prediction", ACM-BCB, 2017, pp. 4503-4722; DOI:10.1145/3107411.3107451, vol. 978, No. 1.

Vilar, S., et al., "Drug-drug interaction through molecular structure similarity analysis", J. Am Med Inform Assoc, 2012, pp. 1066-1074; doi:10.1136/amiajnl-2012-000935, vol. 19.

* cited by examiner

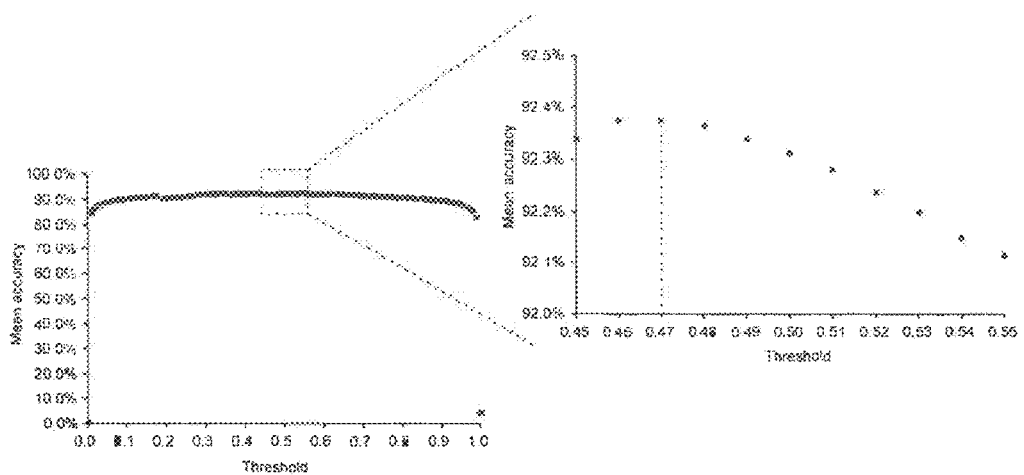

☐ Drug pairs predicted to have only ADEs
☐ Drug pairs predicted to have one or more DDI types in addition to ADEs
☐ Drug pairs not predicted to have ADEs New drug pairs predicted to have no negative health effects Drug pairs reported to have negative health effects ▓ Drugs having same pharmacological action

METHOD FOR PREDICTING DRUG-DRUG OR DRUG-FOOD INTERACTION BY USING STRUCTURAL INFORMATION OF DRUG

CROSS-REFERENCE TO RELATED APPLICATIONS

This application is a U.S. national phase under the provisions of 35 U.S.C. § 371 of International Patent Application No. PCT/KR18/13936 filed Nov. 20, 2018, which in turn claims priority of Korean Patent Application No. 10-2017-0164115 filed Dec. 1, 2017. The disclosures of such international patent application and Korean priority patent application are hereby incorporated herein by reference in their respective entireties, for all purposes.

TECHNICAL FIELD

The present invention relates to a method for predicting a drug-drug interaction and a drug-food interaction using structural information of a drug, and more particularly to a method for predicting the mechanism of action of a drug interaction and drug activity through the result of prediction of a drug interaction expressed as a standardized sentence.

BACKGROUND ART

Drug interaction refers to a change in drug efficacy when two or more drugs are administered together. Drug interaction includes an interaction of a drug with constituents in food.

Drug interactions are important because they can cause serious adverse drug effects (ADEs). Drug interactions have been reported to be associated with up to 30% of all drug side effects (Tatonetti et al., *J. Am. Med. Inf. Assoc.* 19:79-85, 2012; Pirmohamed, M. & Orme, M., Chapman & Hall, London, 1998).

Drug interactions are very important in the pharmaceutical industry because they are known to be the main cause of failure of clinical drug trials. 33 drugs withdrawn from the market since 1990 due to toxicity problems were analyzed with regard to the respective reasons and the result showed that 8 cases (24%) were withdrawn due to drug interactions (Shah R R et al., *Drug Saf.* 27: 145-72, 2004). Guidelines updated by the US FDA in 2012 recommend that inhibition studies on seven types of cytochrome P450 (CYP), including two new types in addition to the existing five types of cytochrome P450 (CYP), be conducted.

However, evaluation of all drug-drug interactions under various conditions is limited due to issues of time and cost. In order to solve this, a methodology for predicting drug interactions has been developed, but there has been no methodology for applying various kinds of interactions to drugs and food ingredients.

Accordingly, as a result of intense efforts to develop a methodology for predicting a drug interaction using only structural information of a drug, the present inventors could reveal the mechanism of adverse drug interactions, the mechanism of action of which is unknown, and could suggest drug combinations that can reduce side effects caused by drug interactions. In addition, the present inventors found that the interaction between a food ingredient and a drug can be predicted using only structural information of the drug, and the activity of the food ingredient can be predicted using a prediction result expressed in the form of a sentence describing an interaction, and completed the present invention based on this finding.

DISCLOSURE

Technical Problem

It is one object of the present invention to provide a method of predicting various types of drug interactions using only structural similarity information of drugs and predicting the action mechanisms of drug-drug interactions and drug-food interactions and drug activity by expressing the prediction results through standardized sentences.

Technical Solution

In accordance with one aspect of the present invention, the above and other objects can be accomplished by the provision of a method of predicting a drug interaction using structural information of a drug, the method comprising calculating a structural similarity profile of each of two compounds of interest for prediction of an interaction therebetween through comparison of a structural similarity between the each compound and any of different predefined compounds, inputting the calculated structural similarity profile of the each of two compounds into a trained model, predicting an interaction between the two compounds by a prediction model using the input structural similarity profile and outputting a result of the prediction in a form of a sentence describing the interaction, and predicting a mechanism of action of the interaction between the two compounds through the output sentence.

In another aspect of the present invention, provided is a device for predicting a drug interaction using structural information of a drug, the device comprising a calculation unit for calculating structural similarity profiles of two compounds of interest for prediction of an interaction therebetween through comparison of a structural similarity, an input unit for combining the calculated structural similarity profiles of the two compounds and inputting a result of the combination, an output unit for predicting an interaction between two compounds using the input structural similarity profile and outputting a result of the prediction in a form of a sentence describing the interaction, and a computation unit for predicting a mechanism of action of the interaction between the two compounds through the output sentence.

In another aspect of the present invention, provided is a method for screening a drug combination having a low probability of adverse interaction using structural information of a drug, the method comprising calculating a structural similarity profile of each of two compounds of interest for prediction of an interaction therebetween through comparison of a structural similarity between the each compound and any of different predefined compounds, inputting the calculated structural similarity profile of the each of two compounds into a trained model, predicting an interaction between the two compounds by a prediction model using the input structural similarity profile, and determining as a combination of compounds having a low probability of adverse interaction when the interaction is not predicted.

DESCRIPTION OF DRAWINGS

FIG. 5 shows the optimal threshold for determining the presence or absence of drug interactions of the present invention.

FIG. 6 shows training conditions used for deep neural network training of the present invention.

BEST MODE

Figure 1:
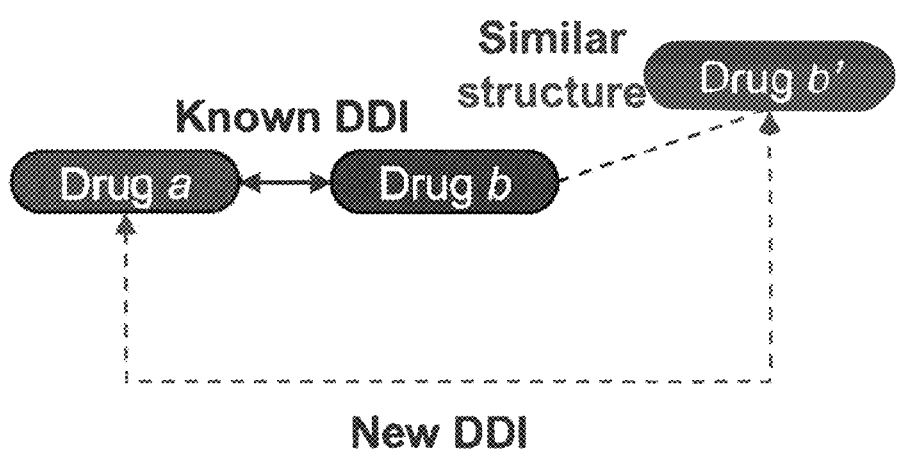
FIG. 1 is a schematic diagram illustrating a conventional principle for predicting a drug interaction based on structural similarity.

Unless defined otherwise, all technical and scientific terms used herein have the same meanings as appreciated by those skilled in the field to which the present invention pertains. In general, the nomenclature used herein is well-known in the art and is ordinarily used.

In the present invention, constructed was a drug interaction prediction model (methodology) that can output interaction-describing sentences when the structural information of two compounds, such as drug-drug and drug-food ingredient, is input through a means of expressing a chemical structure, that is, through a chemical structure file such as SMILES (simplified molecular-input line-entry system), InChI (international chemical identifier), mol and sdf. Such a drug interaction prediction model is capable of predicting a drug interaction by predicting a plurality of interactions of a drug combination based on only structural information of a compound and outputting a result of the prediction in the form of a sentence. The drug interaction prediction method using output in the form of a standardized (predetermined) sentence can be applied to various compounds including food ingredients, and thus is capable of predicting the interaction between the drug and food ingredients as well. In addition, the drug interaction prediction method is capable of predicting new pharmacological activity of the drug and food ingredient using the interaction prediction result.

Thus, in one aspect, the present invention is directed to a method of predicting a drug interaction using structural information of a drug, the method comprising calculating a structural similarity profile of each of two compounds of interest for prediction of an interaction therebetween through comparison of a structural similarity between the each compound and any of different predefined compounds, inputting the calculated structural similarity profile of the each of two compounds into a trained model, predicting an interaction between the two compounds by a prediction model using the input structural similarity profile and outputting a result of the prediction in a form of a sentence describing the interaction, and predicting a mechanism of action of the interaction between the two compounds through the output sentence.

In another aspect, the present invention is directed to a device for predicting a drug interaction using structural information of a drug, the device comprising a calculation unit for calculating structural similarity profiles of two compounds of interest for prediction of an interaction therebetween through comparison of a structural similarity, an input unit for combining the calculated structural similarity profiles of the two compounds and inputting a result of the combination, an output unit for predicting an interaction between two compounds using the input structural similarity profile and outputting a result of the prediction in a form of a sentence describing the interaction, and a computation unit for predicting a mechanism of action of the interaction between the two compounds through the output sentence.

As used herein, the term "prediction" may refer to prediction of a mechanism of a drug interaction, the mechanism of action of which is unknown, and may mean prediction of the activity of a drug or suggestion of a drug combination with reduced side effects.

The mechanism of action may mean a mechanism of action by which one drug changes the efficacy of another drug.

The term "prediction model" used in the present invention to be understood to have the same meaning as "prediction methodology".

As used herein, the term "predefined compounds" refers to a set of a given number of compounds, and this set of compounds refers to a set of compounds used to calculate structural similarity with input compounds of interest for interaction analysis.

The compound structure information used as an input in the present invention can be input in various forms such as character strings (i.e., SMILES, InChI) or files (i.e., mol, sdf) that allow a computer to interpret the structure of the compound.

The "structural similarity" of the present invention can be calculated using various methodologies capable of digitizing the structural similarity between two compounds. Any method of comparing structural similarity may be used, and Tanimoto similarity, Cosine similarity or the like is preferably used.

The "structural similarity profile" of the present invention means a numerical vector obtained by calculating the structural similarity between the structure of each of two input compounds and all approved drugs. Thus, the structural similarity profile of each of the two input compounds is calculated.

As used herein, the term "structural similarity profile" refers to a numerical vector obtained by comparing the structural similarity (value between 0 and 1) between the structure of a single drug and the structure of all of approved drugs. When the total number of approved drugs is 1,000, 1×1000 numerical vectors are obtained from the structural similarity profile of drug a. Since the structures of two compounds are input for drug interaction, 1×1000 and 1×1000 numerical vectors in total are created from two structural similarity profiles.

The expression "combining the two structural similarity profiles" means unifying the structural similarity profiles formed from two compounds. For example, for compounds a and b, a combined structural similarity profile that connects the structural similarity profile of compound a with the structural similarity profile of compound b is formed. That is, it means a numeric vector in the form of 1×2000 (i.e., 1000+1000).

In one embodiment of the present invention, structural similarity profiles of all compounds of interest in determining drug interactions with pre-defined compounds are calculated, and combinations of pairs of drugs between which drug interactions were reported are acquired. Then, the sentence describing the drug interaction is standardized (patterned) and transferred to a classification issue, and the structural similarity profiles corresponding to the combination of two drugs are combined to form a new structural similarity profile representing the interaction between the two drugs, and a drug interaction prediction model is constructed using the standardized interaction-describing sentence.

In the present invention, the calculation of the structural similarity profile may be characterized using Equation 1 or Equation 2 below.

$$\text{Tanimoto coefficient } (a, a') = \frac{|a \cap a'|}{|a \cup a'|} \quad [\text{Equation 1}]$$

$$\text{Cosine similarity } (a, a') = \frac{|a \cdot a|}{\|a\| \|a'\|} \quad [\text{Equation 2}]$$

The method of predicting a drug interaction of the present invention may be characterized in that the output unit outputs the potential of each interaction at a probability between 0 and 1 and when an output probability is 0.47 or less, the potential for a drug interaction is determined to be low. That is, when the output is 0.47 or less of a drug interaction probability and thus an interaction is not predicted, it can be interpreted that a combination of the compounds has a low probability of adverse interactions (less side effects).

In the present invention, the sentence describing the interaction preferably represented by the 86 sentences set forth in Table 1 of Example 1, but is not limited thereto, and can be extended to more than 86 sentences through training.

Since the number of sentences is determined by the data used to train the prediction model, 86 interactions can be predicted and expressed in sentences based on the result of a model trained using 86 drug interaction sentence data. When more than 86 interaction sentences can be obtained through accumulation of more data, more than 86 drug interactions can be predicted and expressed in sentences.

In the present invention, the step of outputting the structural similarity profile in the form of an interaction-describing sentence will be described in detail. The training model of the present invention is trained with drug interaction data represented by 86 or more predetermined standardized sentences. At this time, when structural information of two compounds a and b (drug or food ingredient) in need of interaction prediction is input, the potential of each of 86 or more interactions is shown as a value between 0 and 1. Then, the names of drugs a and b are put into the sentence corresponding to an interaction having a specific value or more to form a new sentence.

That is, in the present invention, the input and output may be characterized by being based on a deep neural network, the input to the deep neural network is a structural similarity profile of two compounds expressing a drug interaction, and the output from the deep neural network is a sentence describing the interaction between the two compounds.

The "deep neural network" of the present invention refers to an artificial neural network (ANN) that includes a plurality of hidden layers between an input layer and an output layer, and the deep neural network is capable of training of a variety of nonlinear relationships including the plurality of hidden layers.

The present invention can predict the mechanism of action of a drug interaction, the mechanism of action of which is unknown, through the constructed drug interaction prediction model, and may suggest an optimal drug combination that exhibits the same medicinal effect, but does not exhibit an adverse drug interaction, regarding an interaction inducing adverse drug actions.

In the present invention, a case for which an interaction is not predicted is a combination of compounds having a low probability of adverse interaction. When the probability of drug interaction acquired by the output unit is output as a value of 0.47 or less, the potential of drug interaction is determined to be low. That is, the case in which a drug interaction probability of 0.47 or less is output, and thus an interaction is not predicted, may be considered to be a combination of compounds having a low probability of adverse interactions (fewer side effects).

The present invention is also capable of predicting various drug interactions between various compounds including food ingredients and approved drugs through the constructed drug interaction prediction model, predicting various interactions that may occur when taking food ingredients and drugs in combination using the sentence-type results of the predicted interaction between food ingredients and drugs, and predicting the activity of various compounds including drugs and food ingredients as well.

In the present invention, the compound is preferably a drug or food ingredient, but is not limited thereto.

In the present invention, the interaction is preferably a mechanism of action or activity information, but is not limited thereto.

The present invention is capable of quickly and accurately predicting interactions occurring in large amounts of drugs and drugs, and in large amounts of drugs and food ingredients, and in particular, helps understanding of the mechanism of action of drug interactions, especially, the mechanism of action of which is unknown, by expressing the results of the interaction prediction in sentences. In addition, the present invention is capable of predicting the activity of an unknown compound using the activity information of the drug expressed in sentences.

In addition, it is possible to screen drugs with fewer side effects through prediction of drug interaction, and it is also possible to design drugs that can avoid unexpected side effects.

Therefore, the present invention is capable of detecting drug interactions early in the drug development stage and thus quickly identifying candidate substances that are expected to have fewer side effects. That is, the present invention is advantageously capable of designing a drug having fewer side effects in the structure optimization phase of drug development. The present invention is also capable of avoiding a drug combination that is expected to cause serious side effects due to drug interactions. In addition, the present invention is capable of predicting activity information of an unknown compound including a drug, thus helping find drug candidates having desired activity without causing serious side effects. These advantages are very useful for industrial applications.

In another aspect, the present invention is directed to a method for screening a drug combination having a low probability of adverse interaction using structural information of a drug, the method comprising calculating a structural similarity profile of each of two compounds of interest for prediction of an interaction therebetween through comparison of a structural similarity between the each compound and any of different predefined compounds, inputting the calculated structural similarity profile of the each of two compounds into a trained model, predicting an interaction between the two compounds by a prediction model using the input structural similarity profile, and determining as a combination of compounds having a low probability of adverse interaction when the interaction is not predicted.

That is, in the case in which an adverse interaction between drug A and drug b is known, when drug B is substituted with drug C having the same pharmaceutical effect as drug B, an adverse interaction between drug A and drug C is not predicted through the method and device of the present invention.

In the present invention, a case for which an interaction is not predicted is a combination of compounds having a low probability of adverse interaction. When the probability of drug interaction acquired by the output unit is output as a value of 0.47 or less, the potential of drug interaction is determined to be low. That is, the case in which a drug interaction probability of 0.47 or less is output and thus an interaction is not predicted may be considered to pertain to a combination of compounds having a low probability of adverse interactions (fewer side effects).

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1: Development of Drug Interaction Prediction Model 1-1: Principles of Drug Interaction Prediction The drug interaction prediction method of the present invention is based on the principle of a method using structural similarity. According to this principle, when an interaction between drug a and drug b is known and drug b' has a similar structure to drug b, drug a and drug b' are presumed to have similar interactions (FIG. 1). A structural similarity profile is used due to the difficulty in specifying the critical (limit) point of a certain structural similarity and the goal of using a greater variety of structural information.

1-2: Calculation of Structural Similarity Profile of a Drug

Figure 2:
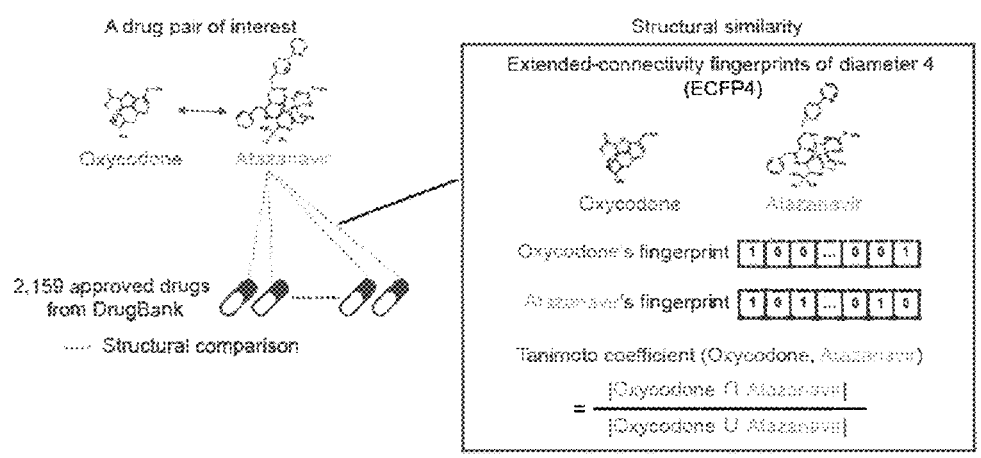
FIG. 2 is a schematic diagram illustrating a process of expressing the interaction between two drugs based on a structural similarity profile.

The structural similarity profile of a single drug is an array obtained as a similarity value obtained by comparing the structural similarity between the drug and 2,159 approved drugs (FIG. 2). In this example, structural similarity was calculated using a Tanimoto coefficient, depicted by the following Equation 1, to measure the similarity.

$$\text{Tanimoto coefficient } (a, a') = \frac{|a \cap a'|}{|a \cup a'|} \quad \text{[Equation 1]}$$

Two drugs are involved in a single drug interaction. To express this, a combined form of two structural similarity profiles obtained from two drugs was used (FIG. 2).

1-3: Acquirement of Drug Interaction Training Data and Expression of Data in Sentences To construct a model for predicting a drug interaction, drug interaction information was obtained from DrugBank. A total of 191,878 drug combinations corresponding to 192,284 drug interactions were obtained. Then, 86 sentences to describe drug interactions were classified (Table 1). The issue of predicting a drug interaction can be defined as a classification issue by renumbering a sentence that describes the interaction.

TABLE 1

| Interaction No. | Sentence describing interaction |
|---|---|
| 1 | Drug a can cause a decrease in the absorption of Drug b resulting in a reduced serum concentration and potentially a decrease in efficacy. |
| 2 | Drug a can cause an increase in the absorption of Drug b resulting in an increased serum concentration and potentially a worsening of adverse effects. |
| 3 | The absorption of Drug b can be decreased when combined with Drug a. |
| 4 | The bioavailability of Drug b can be decreased when combined with Drug a. |
| 5 | The bioavailability of Drug b can be increased when combined with Drug a. |
| 6 | The metabolism of Drug b can be decreased when combined with Drug a. |
| 7 | The metabolism of Drug b can be increased when combined with Drug a. |
| 8 | The protein binding of Drug b can be decreased when combined with Drug a. |
| 9 | The serum concentration of Drug b can be decreased when it is combined with Drug a. |
| 10 | The serum concentration of Drug b can be increased when it is combined with Drug a. |
| 11 | The serum concentration of the active metabolites of Drug b can be increased when Drug b is used in combination with Drug a. |
| 12 | The serum concentration of the active metabolites of Drug b can be reduced when Drug b is used in combination with Drug a resulting in a loss in efficacy. |
| 13 | The therapeutic efficacy of Drug b can be decreased when used in combination with Drug a. |

TABLE 1-continued

| Interaction No. | Sentence describing interaction |
|---|---|
| 14 | The therapeutic efficacy of Drug b can be increased when used in combination with Drug a. |
| 15 | Drug a may decrease the excretion rate of Drug b which could result in a higher serum level. |
| 16 | Drug a may increase the excretion rate of Drug b which could result in a lower serum level and potentially a reduction in efficacy. |
| 17 | Drug a may decrease the cardiotoxic activities of Drug b. |
| 18 | Drug a may increase the cardiotoxic activities of Drug b. |
| 19 | Drug a may increase the central neurotoxic activities of Drug b. |
| 20 | Drug a may increase the hepatotoxic activities of Drug b. |
| 21 | Drug a may increase the nephrotoxic activities of Drug b. |
| 22 | Drug a may increase the neurotoxic activities of Drug b. |
| 23 | Drug a may increase the ototoxic activities of Drug b. |
| 24 | Drug a may decrease effectiveness of Drug b as a diagnostic agent. |
| 25 | The risk of a hypersensitivity reaction to Drug b is increased when it is combined with Drug a. |
| 26 | The risk or severity of adverse effects can be increased when Drug a is combined with Drug b. |
| 27 | The risk or severity of bleeding can be increased when Drug a is combined with Drug b. |
| 28 | The risk or severity of heart failure can be increased when Drug b is combined with Drug a. |
| 29 | The risk or severity of hyperkalemia can be increased when Drug a is combined with Drug b. |
| 30 | The risk or severity of hypertension can be increased when Drug b is combined with Drug a. |
| 31 | The risk or severity of hypotension can be increased when Drug a is combined with Drug b. |
| 32 | The risk or severity of QTc prolongation can be increased when Drug a is combined with Drug b. |
| 33 | Drug a may decrease the analgesic activities of Drug b. |
| 34 | Drug a may decrease the anticoagulant activities of Drug b. |
| 35 | Drug a may decrease the antihypertensive activities of Drug b. |
| 36 | Drug a may decrease the antiplatelet activities of Drug b. |
| 37 | Drug a may decrease the bronchodilatory activities of Drug b. |
| 38 | Drug a may decrease the diuretic activities of Drug b. |
| 39 | Drug a may decrease the neuromuscular blocking activities of Drug b. |
| 40 | Drug a may decrease the sedative activities of Drug b. |
| 41 | Drug a may decrease the stimulatory activities of Drug b. |
| 42 | Drug a may decrease the vasoconstricting activities of Drug b. |
| 43 | Drug a may increase the adverse neuromuscular activities of Drug b. |
| 44 | Drug a may increase the analgesic activities of Drug b. |
| 45 | Drug a may increase the anticholinergic activities of Drug b. |
| 46 | Drug a may increase the anticoagulant activities of Drug b. |
| 47 | Drug a may increase the antihypertensive activities of Drug b. |
| 48 | Drug a may increase the antiplatelet activities of Drug b. |
| 49 | Drug a may increase the antipsychotic activities of Drug b. |
| 50 | Drug a may increase the arrhythmogenic activities of Drug b. |
| 51 | Drug a may increase the atrioventricular blocking (AV block) activities of Drug b. |
| 52 | Drug a may increase the bradycardic activities of Drug b. |
| 53 | Drug a may increase the bronchoconstrictory activities of Drug b. |
| 54 | Drug a may increase the central nervous system depressant (CNS depressant) activities of Drug b. |
| 55 | Drug a may increase the central nervous system depressant (CNS depressant) and hypertensive activities of Drug b. |
| 56 | Drug a may increase the constipating activities of Drug b. |
| 57 | Drug a may increase the dermatologic adverse activities of Drug b. |
| 58 | Drug a may increase the fluid retaining activities of Drug b. |
| 59 | Drug a may increase the hypercalcemic activities of Drug b. |
| 60 | Drug a may increase the hyperglycemic activities of Drug b. |
| 61 | Drug a may increase the hyperkalemic activities of Drug b. |
| 62 | Drug a may increase the hypertensive activities of Drug b. |
| 63 | Drug a may increase the hypocalcemic activities of Drug b. |
| 64 | Drug a may increase the hypoglycemic activities of Drug b. |
| 65 | Drug a may increase the hypokalemic activities of Drug b. |
| 66 | Drug a may increase the hyponatremic activities of Drug b. |
| 67 | Drug a may increase the hypotensive activities of Drug b. |
| 68 | Drug a may increase the hypotensive and central nervous system depressant (CNS depressant) activities of Drug b. |
| 69 | Drug a may increase the immunosuppressive activities of Drug b. |
| 70 | Drug a may increase the myelosuppressive activities of Drug b. |
| 71 | Drug a may increase the myopathic rhabdomyolysis activities of Drug b. |
| 72 | Drug a may increase the neuroexcitatory activities of Drug b. |
| 73 | Drug a may increase the neuromuscular blocking activities of Drug b. |
| 74 | Drug a may increase the orthostatic hypotensive activities of Drug b. |
| 75 | Drug a may increase the photosensitizing activities of Drug b. |
| 76 | Drug a may increase the QTc-prolonging activities of Drug b. |

TABLE 1-continued

| Interaction No. | Sentence describing interaction |
| --- | --- |
| 77 | Drug a may increase the respiratory depressant activities of Drug b. |
| 78 | Drug a may increase the sedative activities of Drug b. |
| 79 | Drug a may increase the serotonergic activities of Drug b. |
| 80 | Drug a may increase the stimulatory activities of Drug b. |
| 81 | Drug a may increase the tachycardic activities of Drug b. |
| 82 | Drug a may increase the thrombogenic activities of Drug b. |
| 83 | Drug a may increase the ulcerogenic activities of Drug b. |
| 84 | Drug a may increase the vasoconstricting activities of Drug b. |
| 85 | Drug a may increase the vasodilatory activities of Drug b. |
| 86 | Drug a may increase the vasopressor activities of Drug b. |

1-4: Construction of Drug Interaction Prediction Model

Figure 3:
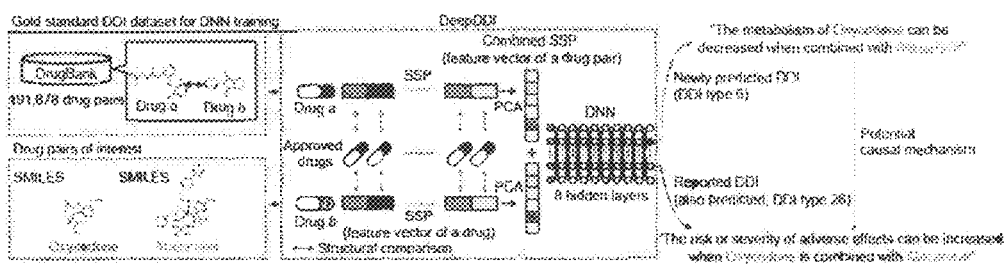
FIG. 3 is a schematic diagram illustrating a prediction model (methodology) proposed by the present invention.

The drug interaction prediction model was constructed using the drug interaction data obtained above. The drug interaction prediction model was built using deep-neural-network-based mechanical training method. Deep neural network was trained using Keras and TensorFlow (Google). As an input to the deep neural network, the structural similarity profiles of two drugs expressing a drug interaction were taken as inputs and 86 drug interactions were shown as results (FIG. 3). At this time, since the two drugs might be involved in several interactions, a prediction model was implemented using a multiple classification issue.

Figure 4:
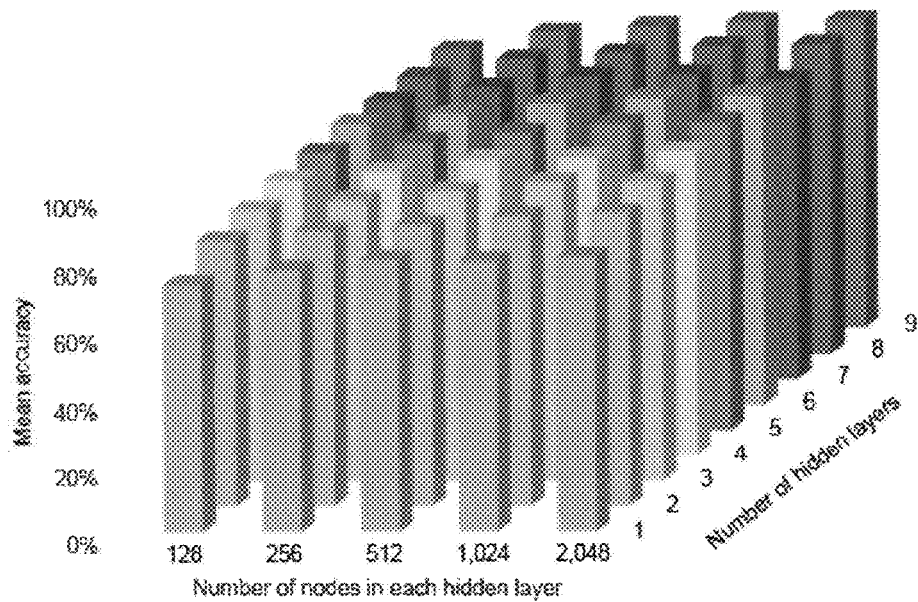
FIG. 4 shows an optimal structure having the highest accuracy among various deep neural network structures.

The results of prediction of the interaction were expressed as the sentences defined in Table 1 corresponding to respective interactions. In order to optimize the structure of the deep neural network, a structure of a deep neural network having 8 hidden layers with the highest accuracy and 2,048 hidden nodes in each hidden layer was selected. For this, 60% of the data were used for training, and 20% of the data were used for evaluation. (FIG. 4). In addition, the probability of drug interaction is expressed as a value between 0 and 1, and the optimal threshold value at which the drug interaction prediction accuracy was maximized was calculated. When the presence or absence of a drug interaction was determined on the basis of a probability of 0.47, the best prediction result was shown (FIG. 5). Various parameter conditions used at this time are shown in FIG. 6. The remaining 20% of data was used to calculate the accuracy of the prediction model after selecting the final model.

Figure 7:
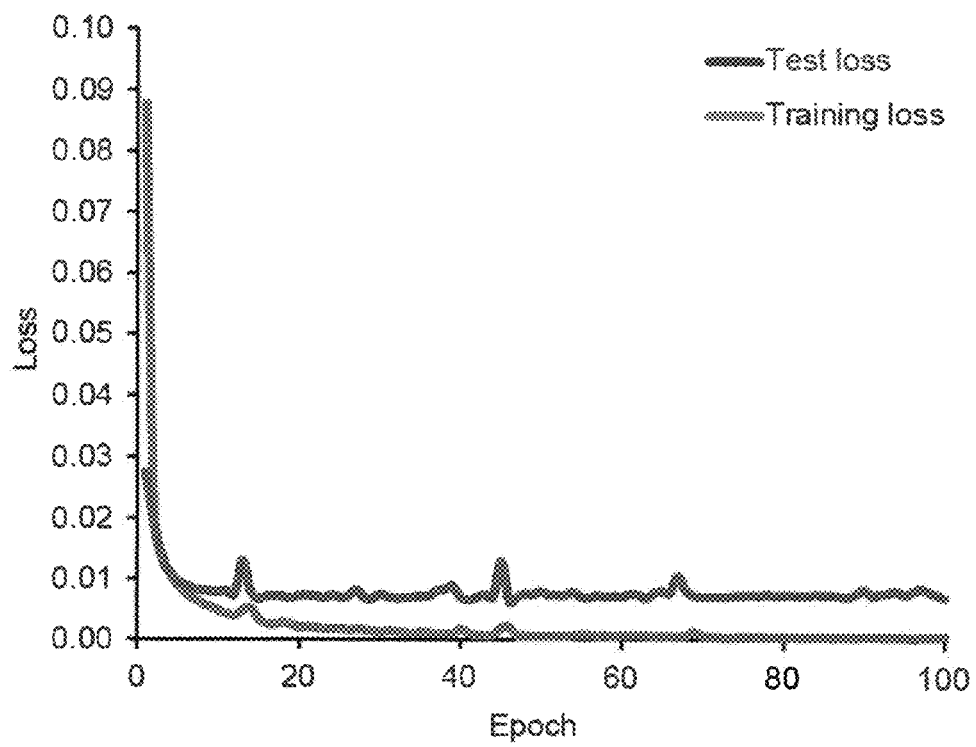
FIG. 7 shows that training errors are reduced as deep neural network training progresses.
Figure 8:
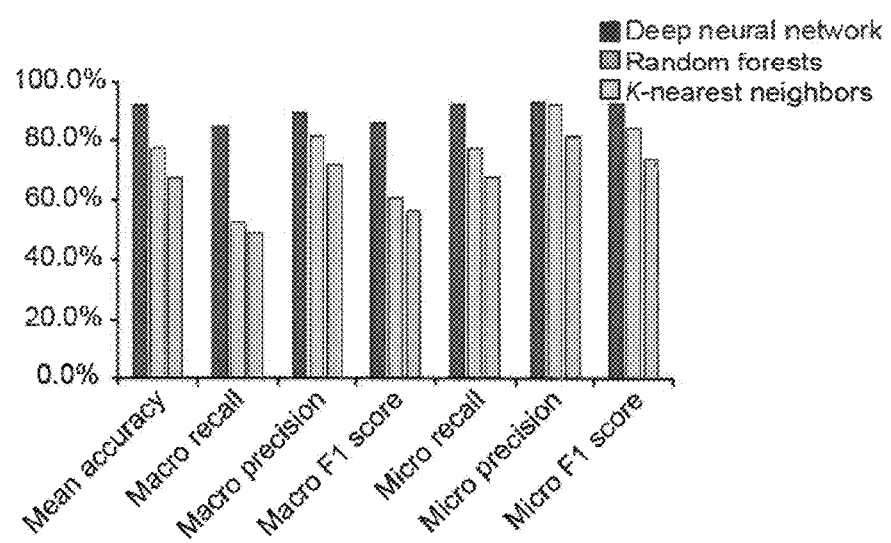
FIG. 8 is a graph showing the accuracy of the prediction method of the present invention.

The result of confirming the distribution of errors in the training process of the interaction prediction model showed that training was performed well without overfitting (FIG. 7). The final interaction prediction accuracy was evaluated to be 92.4% (FIG. 8).

1-5: Comparison Between Structural Similarity Profile Performance

Structural-similarity-profile-based methodology, which is a method for representing drug interactions proposed in the present invention as numerical vectors, is compared with three methods, namely, molecular descriptor, mol2vec (Jaeger S et al., *J. Chem. Inf. Model.* 58(1): 27-35, 2018), and molecular autoencoder (Gomez-Bombarelli R, et al. *ACS Cent. Sci.* 4(2):268-276, 2018).

Figure 9:
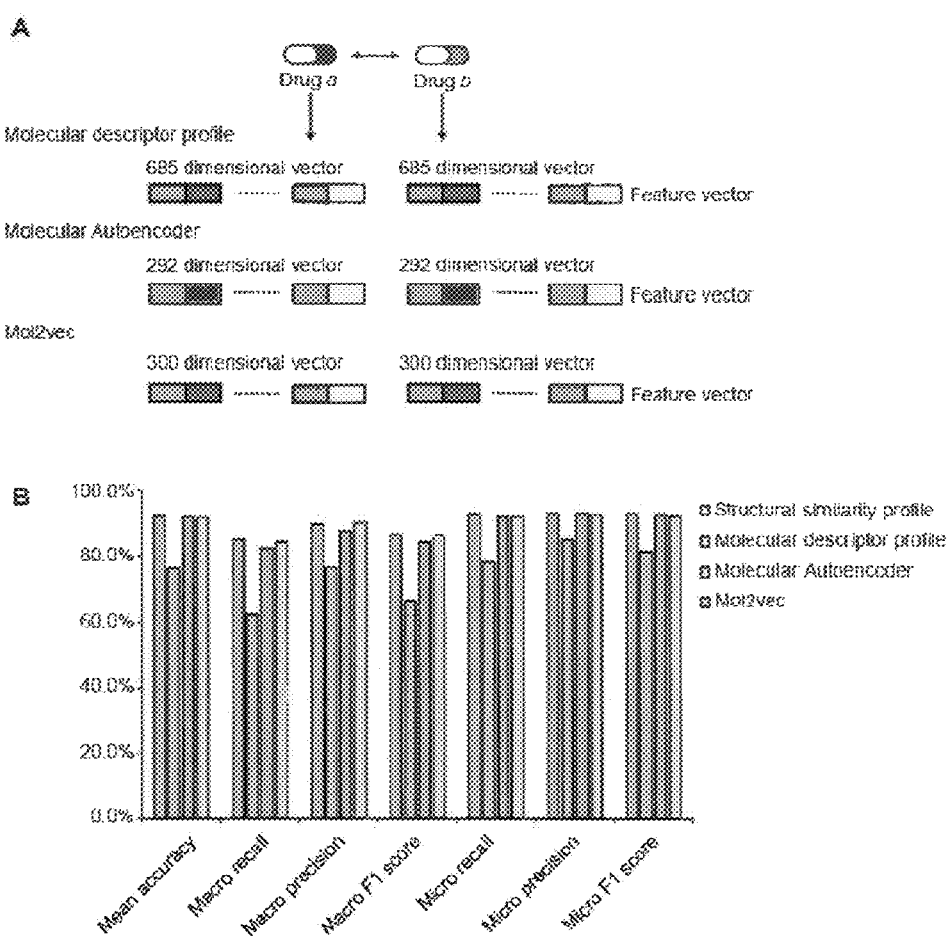
FIG. 9 is a graph for comparing the accuracy between the structural similarity profile used in the prediction method of the present invention and that of other methodology.

As a result, the interaction prediction model based on the structural similarity profile that requires the most intuitive and simple calculation showed the most accurate results (FIG. 9).

Example 2: Prediction of Mechanism of Action of Unknown Interactions Using Drug Interaction Prediction Model (Methodology)

Figure 10:
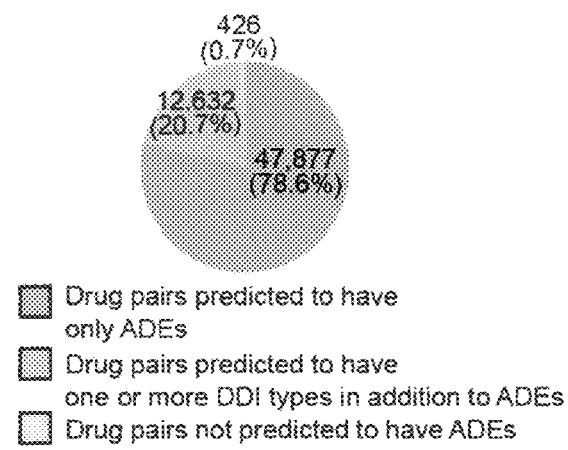
FIG. 10 shows that multiple interactions can simultaneously be predicted based on the result of prediction by the prediction method of the present invention.

2-1: Prediction of all Possible Drug Interactions 2,329,561 possible drug-drug interactions between all approved 2,159 drugs were predicted using the drug interaction prediction model (methodology) constructed in Example 1. Of these, 487,632 drug combinations were not previously reported, but are predicted to be highly likely to interact (FIG. 10).

2-2: Prediction and Verification of Mechanism of Action of Adverse Drug Interactions In the interaction prediction training data obtained from DrugBank, a total of 60,509 drug combinations have been reported to be adverse, but there is no information as to the mechanism of action. It was analyzed whether or not all interaction prediction results obtained in Example 2-1 could explain the mechanism of action of these drug side effects.

Figure 11:
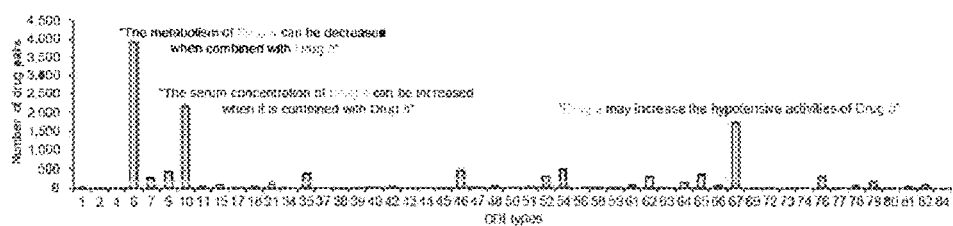
FIG. 11 shows that the prediction method of the present invention exhibits an expected mechanism of an unknown side effect of drug interactions.

As a result, a total of 12,632 drug combinations were predicted to have one of 86 drug interactions other than side effects (FIG. 11). The predicted drug interactions were mostly related to drug metabolism, that is, increased or decreased concentrations in serum (FIG. 11).

In order to verify the prediction results, the 12,632 drug combinations were compared with results from Drugs.com, which is a database that provides information on drug interactions. Information on 182 drug combinations among the 12,632 drug combinations was present at Drugs.com. Among them, 43 drug interactions were found to be consistent with the interactions predicted in Example 2-1.

TABLE 2

| Drug combination name | Predicted drug interaction |
| --- | --- |
| Amiloride; Enalapril | Amiloride may increase the hyperkalemic activities of Enalapril. |
| Amiloride; Lisinopril | Amiloride may increase the hyperkalemic activities of Lisinopril. |
| Amiloride; Ramipril | Amiloride may increase the hyperkalemic activities of Ramipril. |
| Amiloride; Trandolapril | Amiloride may increase the hyperkalemic activities of Trandolapril. |
| Amiodarone; Oxycodone | The metabolism of Oxycodone can be decreased when combined with Amiodarone. |

TABLE 2-continued

| Drug combination name | Predicted drug interaction |
| --- | --- |
| Amitriptyline; Citalopram | Amitriptyline may increase the QTc-prolonging activities of Citalopram. |
| Amitriptyline; Escitalopram | Amitriptyline may increase the QTc-prolonging activities of Escitalopram. |
| Amoxapine; Citalopram | Amoxapine may increase the QTc-prolonging activities of Citalopram. |
| Amoxapine; Escitalopram | Amoxapine may increase the QTc-prolonging activities of Escitalopram. |
| Amprenavir; Temsirolimus | The serum concentration of Temsirolimus can be increased when it is combined with Amprenavir. |
| Anagrelide; Apixaban | Anagrelide may increase the anticoagulant activities of Apixaban. |
| Aprepitant; Oxycodone | The serum concentration of Oxycodone can be increased when it is combined with Aprepitant. |
| Aripiprazole; Tetrabenazine | Aripiprazole may increase the QTc-prolonging activities of Tetrabenazine. |
| Atazanavir; Oxycodone | The metabolism of Oxycodone can be decreased when combined with Atazanavir. |
| Atazanavir; Temsirolimus | The serum concentration of Temsirolimus can be increased when it is combined with Atazanavir. |
| Atazanavir; Toremifene | The metabolism of Toremifene can be decreased when combined with Atazanavir. |
| Azilsartan medoxomil; Spironolactone | Azilsartan medoxomil may increase the hyperkalemic activities of Spironolactone. |
| Bepridil; Conivaptan | The serum concentration of Conivaptan can be increased when it is combined with Bepridil. |
| Boceprevir; Oxycodone | The metabolism of Oxycodone can be decreased when combined with Boceprevir. |
| Boceprevir; Temsirolimus | The serum concentration of Temsirolimus can be increased when it is combined with Boceprevir. |
| Boceprevir; Toremifene | The metabolism of Toremifene can be decreased when combined with Boceprevir. |
| Bupropion; Citalopram | The metabolism of Citalopram can be decreased when combined with Bupropion. |
| Bupropion; Fluoxetine | The metabolism of Fluoxetine can be decreased when combined with Bupropion. |
| Bupropion; Fluvoxamine | The metabolism of Fluvoxamine can be decreased when combined with Bupropion. |
| Bupropion; Paroxetine | The metabolism of Paroxetine can be decreased when combined with Bupropion. |
| Cangrelor; Apixaban | Cangrelor may increase the anticoagulant activities of Apixaban. |
| Chlorpromazine; Sotalol | Chlorpromazine may increase the QTc-prolonging activities of Sotalol. |
| Cimetidine; Phenytoin | The serum concentration of Phenytoin can be increased when it is combined with Cimetidine. |
| Clarithromycin; Oxycodone | The metabolism of Oxycodone can be decreased when combined with Clarithromycin. |
| Clarithromycin; Temsirolimus | The serum concentration of Temsirolimus can be increased when it is combined with Clarithromycin. |
| Clomipramine; Lorcaserin | The metabolism of Lorcaserin can be decreased when combined with Clomipramine. |
| Clotrimazole; Oxycodone | The metabolism of Oxycodone can be decreased when combined with Clotrimazole. |
| Clozapine; Sotalol | Clozapine may increase the QTc-prolonging activities of Sotalol. |
| Cobicistat; Oxycodone | The serum concentration of Oxycodone can be increased when it is combined with Cobicistat. |
| Cobicistat; Toremifene | The serum concentration of Toremifene can be increased when it is combined with Cobicistat. |
| Cobicistat; Toremifene | The serum concentration of Toremifene can be increased when it is combined with Cobicistat. |
| Conivaptan; Flibanserin | The serum concentration of Flibanserin can be increased when it is combined with Conivaptan. |
| Crizotinib; Flibanserin | The serum concentration of Flibanserin can be increased when it is combined with Crizotinib. |
| Crizotinib; Oxycodone | The metabolism of Oxycodone can be decreased when combined with Crizotinib. |
| Darunavir; Oxycodone | The serum concentration of Oxycodone can be increased when it is combined with Darunavir. |
| Delavirdine; Oxycodone | The metabolism of Oxycodone can be decreased when combined with Delavirdine. |
| Desipramine; Citalopram | Desipramine may increase the QTc-prolonging activities of Citalopram. |
| Desipramine; Escitalopram | Desipramine may increase the QTc-prolonging activities of Escitalopram. |
| Desipramine; Lorcaserin | The metabolism of Lorcaserin can be decreased when combined with Desipramine. |

TABLE 2-continued

| Drug combination name | Predicted drug interaction |
| --- | --- |
| Digoxin; Adenosine | Digoxin may decrease the cardiotoxic activities of Adenosine. |
| Diltiazem; Flibanserin | The serum concentration of Flibanserin can be increased when it is combined with Diltiazem. |
| Diltiazem; Guanfacine | The metabolism of Guanfacine can be decreased when combined with Diltiazem. |
| Diltiazem; Oxycodone | The metabolism of Oxycodone can be decreased when combined with Diltiazem. |
| Dipyridamole; Apixaban | Dipyridamole may increase the anticoagulant activities of Apixaban. |
| Doxepin; Isocarboxazid | Doxepin may increase the serotonergic activities of Isocarboxazid. |
| Dronedarone; Oxycodone | The metabolism of Oxycodone can be decreased when combined with Dronedarone. |
| Duloxetine; Pimozide | The serum concentration of Pimozide can be increased when it is combined with Duloxetine. |
| Epoprostenol Apixaban | Epoprostenol may increase the anticoagulant activities of Apixaban. |
| Ergotamine; Bromocriptine | Ergotamine may increase the vasoconstricting activities of Bromocriptine. |
| Ergotamine; Efavirenz | The metabolism of Efavirenz can be decreased when combined with Ergotamine. |
| Erythromycin; Oxycodone | The metabolism of Oxycodone can be decreased when combined with Erythromycin. |
| Fenofibrate; Atorvastatin | The serum concentration of Atorvastatin can be increased when it is combined with Fenofibrate. |
| Fenofibrate; Pitavastatin | The serum concentration of Pitavastatin can be increased when it is combined with Fenofibrate. |
| Fenofibrate; Rosuvastatin | The serum concentration of Rosuvastatin can be increased when it is combined with Fenofibrate. |
| Fluconazole; Oxycodone | The metabolism of Oxycodone can be decreased when combined with Fluconazole. |
| Fluoxetine; Clomipramine | The serum concentration of Clomipramine can be increased when it is combined with Fluoxetine. |
| Fluoxetine; Desipramine | The serum concentration of Desipramine can be increased when it is combined with Fluoxetine. |
| Fluoxetine; Doxepin | The serum concentration of Doxepin can be increased when it is combined with Fluoxetine. |
| Fluoxetine; Droperidol | Fluoxetine may increase the QTc-prolonging activities of Droperidol. |
| Fluoxetine; Imipramine | The serum concentration of Imipramine can be increased when it is combined with Fluoxetine. |
| Fluvoxamine; Amitriptyline | The metabolism of Amitriptyline can be decreased when combined with Fluvoxamine. |
| Fluvoxamine; Amoxapine | The metabolism of Amoxapine can be decreased when combined with Fluvoxamine. |
| Fluvoxamine; Clomipramine | The metabolism of Clomipramine can be decreased when combined with Fluvoxamine. |
| Fluvoxamine; Clopidogrel | The metabolism of Clopidogrel can be decreased when combined with Fluvoxamine. |
| Fluvoxamine; Desipramine | The metabolism of Desipramine can be decreased when combined with Fluvoxamine. |
| Fluvoxamine; Doxepin | The metabolism of Doxepin can be decreased when combined with Fluvoxamine. |
| Fluvoxamine; Imipramine | The metabolism of Imipramine can be decreased when combined with Fluvoxamine. |
| Fluvoxamine; Nortriptyline | The metabolism of Nortriptyline can be decreased when combined with Fluvoxamine. |
| Fluvoxamine; Protriptyline | The metabolism of Protriptyline can be decreased when combined with Fluvoxamine. |
| Fosamprenavir; Flibanserin | The serum concentration of Flibanserin can be increased when it is combined with Fosamprenavir. |
| Fosamprenavir; Oxycodone | The metabolism of Oxycodone can be decreased when combined with Fosamprenavir. |
| Fosamprenavir; Temsirolimus | The metabolism of Temsirolimus can be decreased when combined with Fosamprenavir. |
| Furazolidone; Bupropion | Furazolidone may increase the hypertensive activities of Bupropion. |
| Furazolidone; Maprotiline | Furazolidone may increase the serotonergic activities of Maprotiline. |
| Furazolidone; Phenylpropanolamine | Furazolidone may increase the hypertensive activities of Phenylpropanolamine. |
| Halothane; Arsenic trioxide | Halothane may increase the QTc-prolonging activities of Arsenic trioxide. |
| Halothane; Escitalopram | Halothane may increase the QTc-prolonging activities of Escitalopram. |
| Halothane; Iloperidone | Halothane may increase the QTc-prolonging activities of Iloperidone. |

TABLE 2-continued

| Drug combination name | Predicted drug interaction |
| --- | --- |
| Halothane; Pimozide | Halothane may increase the QTc-prolonging activities of Pimozide. |
| Halothane; Sotalol | Halothane may increase the QTc-prolonging activities of Sotalol. |
| Ibrutinib; Warfarin | Ibrutinib may increase the anticoagulant activities of Warfarin. |
| Idelalisib; Oxycodone | The metabolism of Oxycodone can be decreased when combined with Idelalisib. |
| Idelalisib; Toremifene | The metabolism of Toremifene can be decreased when combined with Idelalisib. |
| Iloprost; Apixaban | Iloprost may increase the anticoagulant activities of Apixaban. |
| Imipramine; Lorcaserin | The metabolism of Lorcaserin can be decreased when combined with Imipramine. |
| Indinavir; Oxycodone | The metabolism of Oxycodone can be decreased when combined with Indinavir. |
| Indinavir; Temsirolimus | The serum concentration of Temsirolimus can be increased when it is combined with Indinavir. |
| Indinavir; Toremifene | The metabolism of Toremifene can be decreased when combined with Indinavir. |
| Isavuconazonium; Flibanserin | The serum concentration of Flibanserin can be increased when it is combined with Isavuconazonium. |
| Isavuconazonium; Oxycodone | The metabolism of Oxycodone can be decreased when combined with Isavuconazonium. |
| Isocarboxazid; Bupropion | Isocarboxazid may increase the hypertensive activities of Bupropion. |
| Isocarboxazid; Hydrocodone | Isocarboxazid may increase the central nervous system depressant (CNS depressant) activities of Hydrocodone. |
| Isocarboxazid; Phenylpropanolamine | Isocarboxazid may increase the hypertensive activities of Phenylpropanolamine. |
| Itraconazole; Bepridil | The metabolism of Bepridil can be decreased when combined with Itraconazole. |
| Itraconazole; Oxycodone | The metabolism of Oxycodone can be decreased when combined with Itraconazole. |
| Itraconazole; Toremifene | The metabolism of Toremifene can be decreased when combined with Itraconazole. |
| Ketoconazole; Oxycodone | The metabolism of Oxycodone can be decreased when combined with Ketoconazole. |
| Ketoconazole; Toremifene | The metabolism of Toremifene can be decreased when combined with Ketoconazole. |
| Leflunomide; Fingolimod | Leflunomide may increase the immunosuppressive activities of Fingolimod. |
| Leflunomide; Tofacitinib | Leflunomide may increase the immunosuppressive activities of Tofacitinib. |
| Linezolid; Maprotiline | Linezolid may increase the serotonergic activities of Maprotiline. |
| Lomitapide; Atorvastatin | The serum concentration of Atorvastatin can be increased when it is combined with Lomitapide. |
| Naproxen; Apixaban | Naproxen may increase the anticoagulant activities of Apixaban. |
| Nefazodone; Atorvastatin | The metabolism of Atorvastatin can be decreased when combined with Nefazodone. |
| Nefazodone; Oxycodone | The metabolism of Oxycodone can be decreased when combined with Nefazodone. |
| Nefazodone; Toremifene | The metabolism of Toremifene can be decreased when combined with Nefazodone. |
| Nelfinavir; Oxycodone | The metabolism of Oxycodone can be decreased when combined with Nelfinavir. |
| Nelfinavir; Temsirolimus | The serum concentration of Temsirolimus can be increased when it is combined with Nelfinavir. |
| Nelfinavir; Toremifene | The metabolism of Toremifene can be decreased when combined with Nelfinavir. |
| Netupitant; Oxycodone | The serum concentration of Oxycodone can be increased when it is combined with Netupitant. |
| Nortriptyline; Citalopram | Nortriptyline may increase the QTc-prolonging activities of Citalopram. |
| Nortriptyline; Escitalopram | Nortriptyline may increase the QTc-prolonging activities of Escitalopram. |
| Ondansetron; Iloperidone | Ondansetron may increase the QTc-prolonging activities of Iloperidone. |
| Oxycodone; Conivaptan | The serum concentration of Conivaptan can be increased when it is combined with Oxycodone. |
| Paroxetine; Amitriptyline | The metabolism of Amitriptyline can be decreased when combined with Paroxetine. |
| Paroxetine; Amoxapine | The metabolism of Amoxapine can be decreased when combined with Paroxetine. |
| Paroxetine; Clomipramine | The metabolism of Clomipramine can be decreased when combined with Paroxetine. |

TABLE 2-continued

| Drug combination name | Predicted drug interaction |
|---|---|
| Paroxetine; Desipramine | The metabolism of Desipramine can be decreased when combined with Paroxetine. |
| Paroxetine; Imipramine | The metabolism of Imipramine can be decreased when combined with Paroxetine. |
| Paroxetine; Nortriptyline | The metabolism of Nortriptyline can be decreased when combined with Paroxetine. |
| Paroxetine; Trimipramine | The metabolism of Trimipramine can be decreased when combined with Paroxetine. |
| Phenelzine; Bupropion | Phenelzine may increase the hypertensive activities of Bupropion. |
| Phenelzine; Phenylpropanolamine | Phenelzine may increase the hypertensive activities of Phenylpropanolamine. |
| Phenelzine; Rasagiline | Phenelzine may increase the hypertensive activities of Rasagiline. |
| Phenelzine; Selegiline | Phenelzine may increase the hypertensive activities of Selegiline. |
| Posaconazole; Oxycodone | The metabolism of Oxycodone can be decreased when combined with Posaconazole. |
| Posaconazole; Vinorelbine | The metabolism of Vinorelbine can be decreased when combined with Posaconazole. |
| Prasugrel; Apixaban | Prasugrel may increase the anticoagulant activities of Apixaban. |
| Procarbazine; Bupropion | Procarbazine may increase the hypertensive activities of Bupropion. |
| Procarbazine; Lisdexamfetamine | Procarbazine may increase the hypertensive activities of Lisdexamfetamine. |
| Procarbazine; Remifentanil | Procarbazine may increase the hypotensive activities of Remifentanil. |
| Protriptyline; Citalopram | Protriptyline may increase the QTc-prolonging activities of Citalopram. |
| Protriptyline; Escitalopram | Protriptyline may increase the QTc-prolonging activities of Escitalopram. |
| Ranolazine; Oxycodone | The metabolism of Oxycodone can be decreased when combined with Ranolazine. |
| Rasagiline; Bupropion | Rasagiline may increase the hypertensive activities of Bupropion. |
| Rasagiline; Isocarboxazid | Rasagiline may increase the hypotensive activities of Isocarboxazid. |
| Ritonavir; Temsirolimus | The serum concentration of Temsirolimus can be increased when it is combined with Ritonavir. |
| Ritonavir; Triamcinolone | The metabolism of Triamcinolone can be decreased when combined with Ritonavir. |
| Saquinavir; Oxycodone | The metabolism of Oxycodone can be decreased when combined with Saquinavir. |
| Saquinavir; Temsirolimus | The serum concentration of Temsirolimus can be increased when it is combined with Saquinavir. |
| Selegiline; Diethylpropion | Selegiline may increase the hypertensive activities of Diethylpropion. |
| Sevoflurane; Mesoridazine | Sevoflurane may increase the QTc-prolonging activities of Mesoridazine. |
| Spironolactone; Captopril | Spironolactone may increase the hyperkalemic activities of Captopril. |
| Spironolactone; Irbesartan | Spironolactone may increase the hyperkalemic activities of Irbesartan. |
| Spironolactone; Moexipril | Spironolactone may increase the hyperkalemic activities of Moexipril. |
| Tacrolimus; Panobinostat | Tacrolimus may increase the QTc-prolonging activities of Panobinostat. |
| Telaprevir; Amiodarone | The serum concentration of Amiodarone can be increased when it is combined with Telaprevir. |
| Telaprevir; Bepridil | The serum concentration of Bepridil can be increased when it is combined with Telaprevir. |
| Telaprevir; Oxycodone | The metabolism of Oxycodone can be decreased when combined with Telaprevir. |
| Telaprevir; Quinidine | The metabolism of Quinidine can be decreased when combined with Telaprevir. |
| Telaprevir; Temsirolimus | The serum concentration of Temsirolimus can be increased when it is combined with Telaprevir. |
| Telaprevir; Toremifene | The metabolism of Toremifene can be decreased when combined with Telaprevir. |
| Telithromycin; Oxycodone | The metabolism of Oxycodone can be decreased when combined with Telithromycin. |
| Telithromycin; Temsirolimus | The serum concentration of Temsirolimus can be increased when it is combined with Telithromycin. |
| Ticagrelor; Apixaban | Ticagrelor may increase the anticoagulant activities of Apixaban. |
| Tizanidine; Fenoldopam | Tizanidine may increase the hypotensive activities of Fenoldopam. |

TABLE 2-continued

| Drug combination name | Predicted drug interaction |
|---|---|
| Tizanidine; Hydroflumethiazide | Tizanidine may increase the hypotensive activities of Hydroflumethiazide. |
| Tizanidine; Phenoxybenzamine | Tizanidine may increase the hypotensive activities of Phenoxybenzamine. |
| Tizanidine; Phentolamine | Tizanidine may increase the hypotensive activities of Phentolamine. |
| Tizanidine; Tolazoline | Tizanidine may increase the hypotensive activities of Tolazoline. |
| Tranylcypromine; Rasagiline | Tranylcypromine may increase the hypertensive activities of Rasagiline. |
| Trazodone; Methadone | Trazodone may increase the QTc-prolonging activities of Methadone. |
| Triamterene; Enalapril | Triamterene may increase the hyperkalemic activities of Enalapril. |
| Triamterene; Lisinopril | Triamterene may increase the hyperkalemic activities of Lisinopril. |
| Trifluoperazine; Thioridazine | The serum concentration of Thioridazine can be increased when it is combined with Trifluoperazine. |
| Triflupromazine; Thioridazine | The serum concentration of Thioridazine can be increased when it is combined with Triflupromazine. |
| Valsartan; Amiloride | Valsartan may increase the hyperkalemic activities of Amiloride. |
| Verapamil; Bisoprolol | Verapamil may increase the bradycardic activities of Bisoprolol. |
| Verapamil; Flibanserin | The serum concentration of Flibanserin can be increased when it is combined with Verapamil. |
| Verapamil; Guanfacine | The metabolism of Guanfacine can be decreased when combined with Verapamil. |
| Verapamil; Oxycodone | The metabolism of Oxycodone can be decreased when combined with Verapamil. |
| Vorapaxar; Apixaban | Vorapaxar may increase the anticoagulant activities of Apixaban. |
| Vorapaxar; Argatroban | Vorapaxar may increase the anticoagulant activities of Argatroban. |
| Vorapaxar; Bivalirudin | Vorapaxar may increase the anticoagulant activities of Bivalirudin. |
| Vorapaxar; Edoxaban | Vorapaxar may increase the anticoagulant activities of Edoxaban. |
| Voriconazole; Oxycodone | The metabolism of Oxycodone can be decreased when combined with Voriconazole. |
| Voriconazole; Toremifene | The metabolism of Toremifene can be decreased when combined with Voriconazole. |
| Voriconazole; Vinblastine | The metabolism of Vinblastine can be decreased when combined with Voriconazole. |

Figure 12:
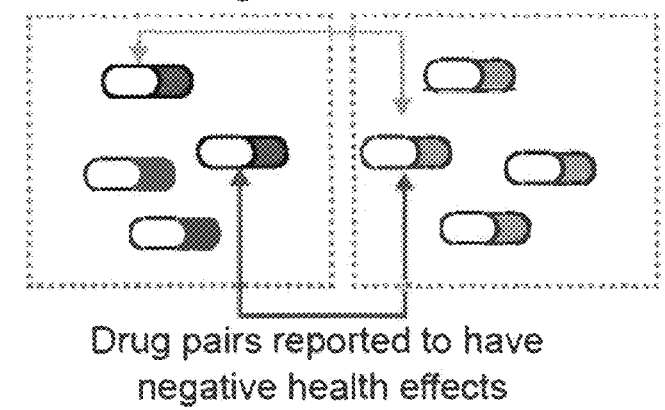
FIG. 12 is a schematic diagram for suggesting a new drug combination that reduces drug side effects caused by drug interactions using the prediction method of the present invention.
Figure 13:
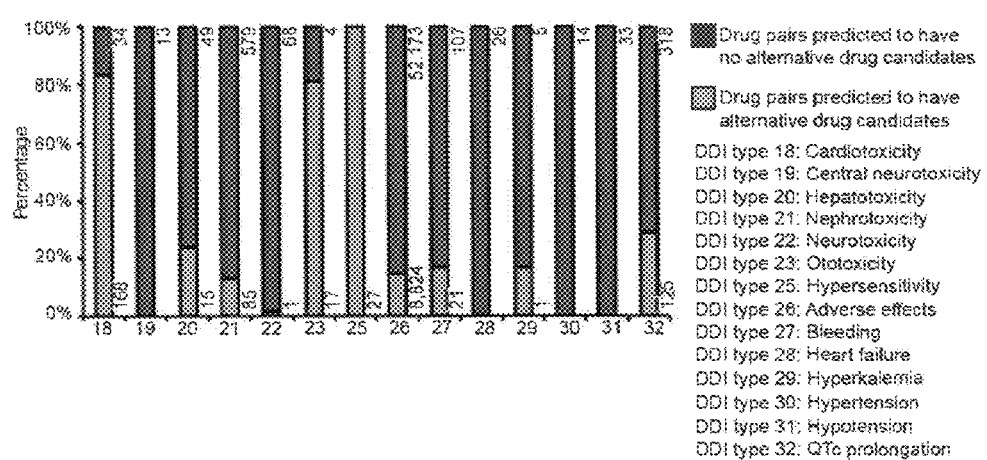
FIG. 13 shows a suggested new drug combination regarding drug interactions harmful to the human body using the prediction method of the present invention.

Example 3: Suggestion of Drug Combinations Having Low Probability of Adverse Interactions Using Drug Interaction Prediction Model Drug combinations that are expected to have no adverse effects while exhibiting the same pharmaceutical efficacy were suggested based on drug interactions that cause known adverse effects using the drug interaction prediction model constructed in Example 1 (FIG. 12). In particular, this was applied to 62,707 drug combinations related to 14 drug interactions clearly found to have adverse drug interactions. The 14 drug interactions included increased cardiotoxicity, increased renal toxicity, and increased risk of drug side effects (FIG. 13).

Figure 14:
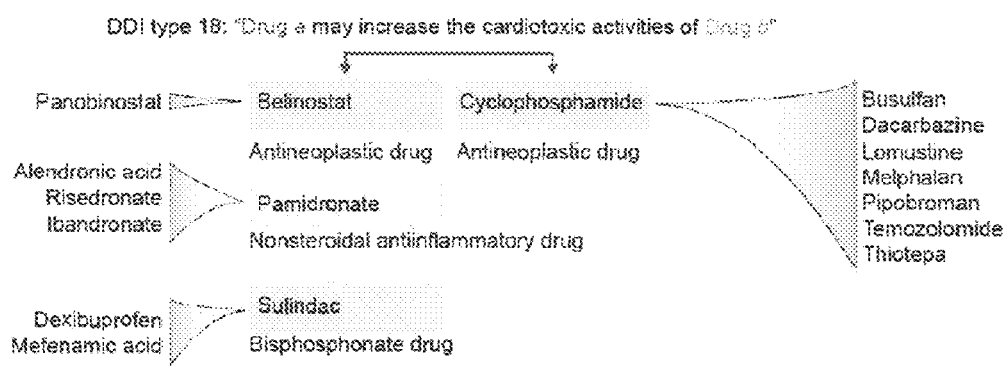
FIG. 14 shows an example of a case in which cardiotoxicity caused by a drug interaction can be reduced.

As a result, it was predicted that 9,284 drug combinations out of a total of 62,707 drug combinations could be replaced with drugs having lower probability of adverse effects. Representatively, 168 drug combinations out of 202 drug combinations reported to increase the likelihood of cardiotoxicity were predicted to have alternative drug candidates. In particular, when the anticancer drug cyclophosphamide is replaced with seven different anticancer drugs, namely busulfan, dacarbazine, lomustine, melphalan, pipobroman, temozolomide or thiotepa, the probability of drug interactions causing cardiotoxicity was predicted to be reduced (FIG. 14).

Figure 15:
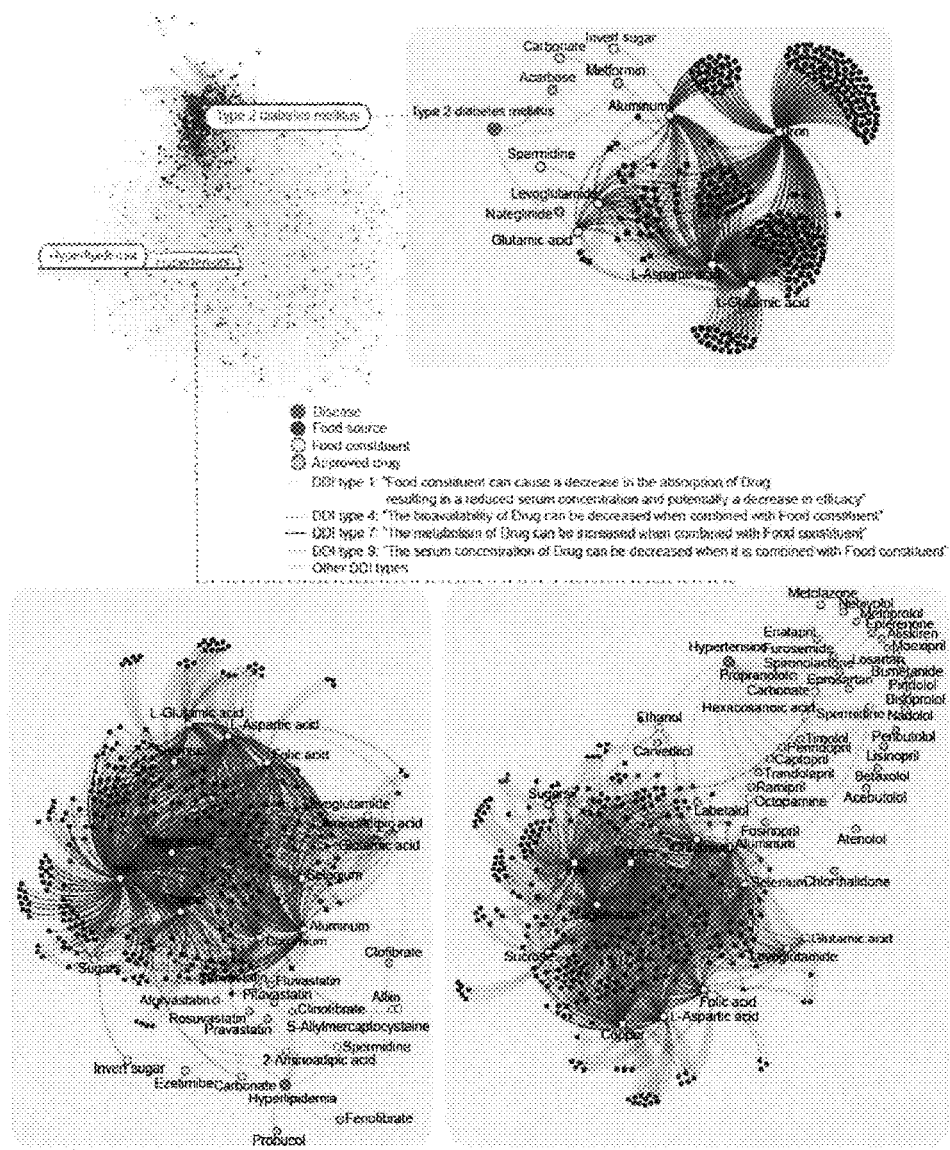
FIG. 15 is a schematic diagram illustrating a method for exploring the activity of a food ingredient using the method of predicting a drug interaction of the present invention.

Example 4: Prediction of Interactions Between Drug and Food Constituents Using Drug Interaction Prediction Model 4-1: Prediction of Drug-Food Interaction The drug interaction prediction model constructed in Example 1 was applied to food ingredients. For this purpose, 1,523 food ingredients were obtained from FooDB (http://foodb.ca/). Interactions of a total of 3,288,157 (2,159 drugs× 1,523 food ingredients) pairs (combinations) of drugs and food ingredients were predicted using the prediction model (FIG. 15).

As a result, 690,956 drug interactions between 319,993 pairs of drugs and food ingredients were predicted. The 690,959 drug interactions are expressed in sentences. Cases where the name of a food ingredient appears as a subject, that is, where the food ingredient affects the pharmaceutical efficacy of the drug, were analyzed. The result showed that 272 food ingredients were predicted to be capable of changing the pharmaceutical efficacy of drugs.

Therefore, in particular, each case in which a food ingredient deteriorates the pharmaceutical efficacy of a drug was analyzed. There were four types of interactions in which a food ingredient deteriorates the pharmaceutical efficacy of the drug, namely decreasing the absorption of a drug, decreasing bioavailability of a drug, decreasing a serum concentration, and increasing metabolism of a drug. It was predicted that a total of 73 food ingredients were capable of reducing the pharmaceutical efficacy of at least one of 430 drugs through one of the four interactions (FIG. 15).

4-2: Prediction of Activity of Food Ingredient Using Drug Interaction Prediction Results The activity information of food ingredients was analyzed using sentences including information associated with the activity of food ingredients, among the prediction results expressing all drug interactions obtained in Example 4-1 in sentences. For example, it can be predicted that a food ingredient has anticoagulant activity from the interaction sentence "drug can reduce the anticoagulant activity of a food ingredient". In particular, in order to provide target information of food ingredients together, food ingredients having a similar structure (Tanimoto coefficient>0.75) to drugs reported to have the same activity were considered in the analysis.

Figure 16:
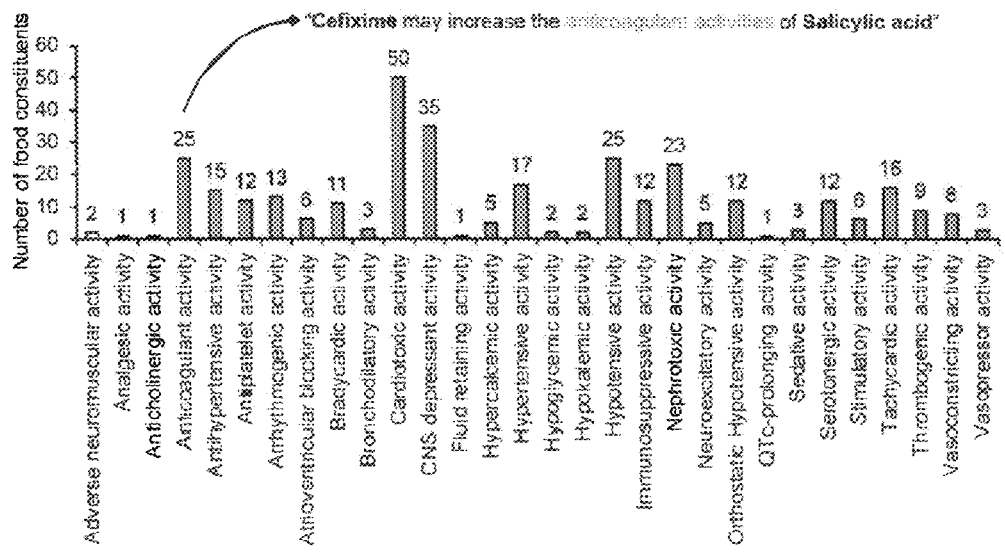
FIG. 16 shows the result of prediction of the activity of the food ingredient using the method of predicting a drug interaction of the present invention.
Figure 17:
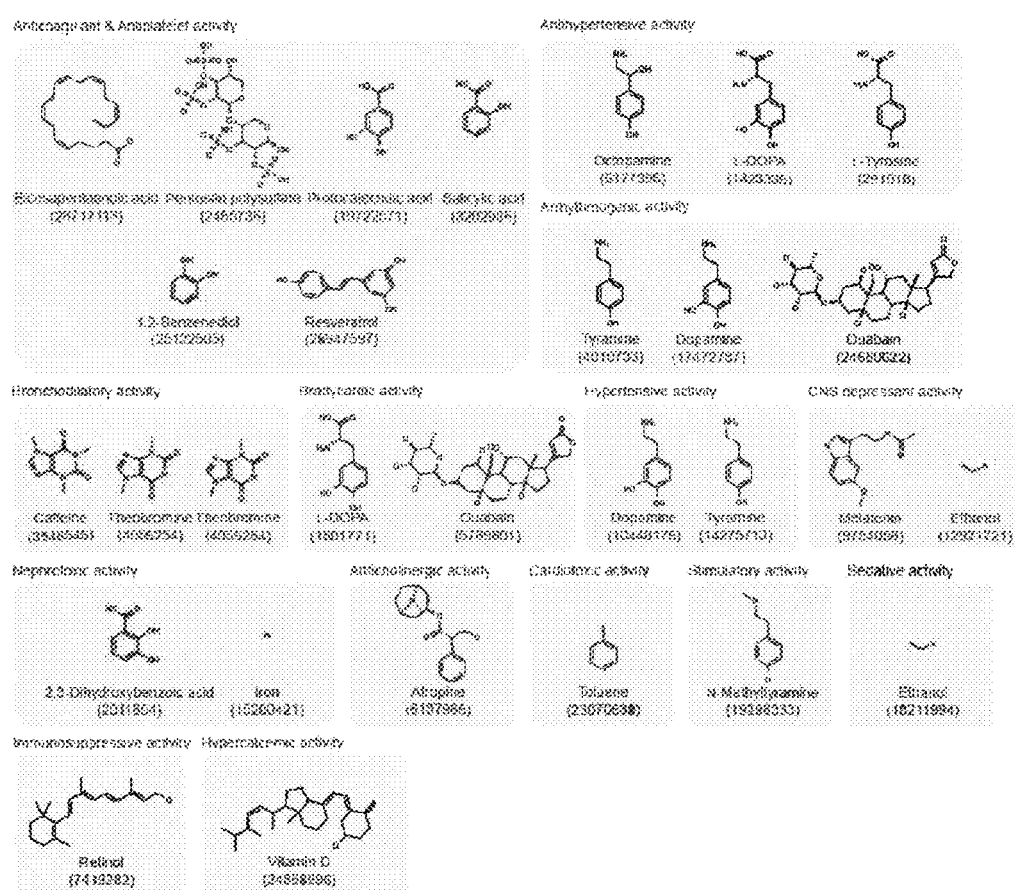
FIG. 17 shows food ingredients with literature evidence among food ingredients, the activity of which is predicted through the drug interaction prediction method.

As a result, 30 types of activities of a total of 149 food ingredients were predicted (FIG. 16). Among the 149 food ingredients, 23 food ingredients were found to have the same activity information as the results of the existing literature (FIG. 17).

INDUSTRIAL APPLICABILITY

The drug interaction prediction method according to the present invention is capable of predicting the drug interaction quickly and accurately, and in particular is capable of predicting activity information of an unknown compound by expressing the prediction results in sentences, thus being very useful for developing drugs that can exhibit desired activity without causing side effects.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

The invention claimed is:

1. A computer-implemented method of predicting a drug interaction using structural information of a drug, the method comprising:

calculating a structural similarity profile of each of two compounds of interest for prediction of an interaction therebetween through comparison of a structural similarity between each compound and any of different predefined compounds by using the following Equation 1 or Equation 2:

$$\text{Tanimoto coefficient}(a, a') = \frac{|a \cap a'|}{|a \cup a'|} \quad \text{[Equation 1]}$$

$$\text{Cosine similarity}(a, a') = \frac{|a \cdot a|}{\|a\| \|a'\|}; \quad \text{[Equation 2]}$$

inputting the calculated structural similarity profile of the each of two compounds into a trained deep neural network model;

predicting an interaction between the two compounds by the deep neural network model using the input structural similarity profile and outputting a result of the prediction in a form of a sentence describing the interaction as shown in the following Table 1:

TABLE 11

| Interaction No. | Sentence describing interaction |
|---|---|
| 1 | Drug a can cause a decrease in the absorption of Drug b resulting in a reduced serum concentration and potentially a decrease in efficacy. |
| 2 | Drug a can cause an increase in the absorption of Drug b resulting in an increased serum concentration and potentially a worsening of adverse effects. |
| 3 | The absorption of Drug b can be decreased when combined with Drug a. |
| 4 | The bioavailability of Drug b can be decreased when combined with Drug a. |
| 5 | The bioavailability of Drug b can be increased when combined with Drug a. |
| 6 | The metabolism of Drug b can be decreased when combined with Drug a |
| 7 | The metabolism of Drug b can be increased when combined with Drug a |
| 8 | The protein binding of Drug b can be decreased when combined with Drug a. |
| 9 | The serum concentration of Drug b can be decreased when it is combined with Drug a. |
| 10 | The serum concentration of Drug b can be increased when it is combined with Drug a. |
| 11 | The serum concentration of the active metabolites of Drug b can be increased when Drug b is used in combination with Drug a. |
| 12 | The serum concentration of the active metabolites of Drug b can be reduced when Drug b is used in combination with Drug a resulting in a loss in efficacy. |
| 13 | The therapeutic efficacy of Drug b can be decreased when used in combination with Drug a. |
| 14 | The therapeutic efficacy of Drug b can be increased when used in combination with Drug a. |
| 15 | Drug a may decrease the excretion rate of Drug b which could result in a higher serum level. |
| 16 | Drug a may increase the excretion rate of Drug b which could result in a lower serum level and potentially a reduction in efficacy. |
| 17 | Drug a may decrease the cardiotoxic activities of Drug b. |
| 18 | Drug a may increase the cardiotoxic activities of Drug b. |
| 19 | Drug a may increase the central neurotoxic activities of Drug b. |
| 20 | Drug a may increase the hepatotoxic activities of Drug b. |
| 21 | Drug a may increase the nephrotoxic activities of Drug b. |
| 22 | Drug a may increase the neurotoxic activities of Drug b. |
| 23 | Drug a may increase the ototoxic activities of Drug b. |
| 24 | Drug a may decrease effectiveness of Drug b as a diagnostic agent. |
| 25 | The risk of a hypersensitivity reaction to Drug b is increased when it is combined with Drug a. |
| 26 | The risk or severity of adverse effects can be increased when Drug a is combined with Drug b. |
| 27 | The risk or severity of bleeding can be increased when Drug a is combined with Drug b. |
| 28 | The risk or severity of heart failure can be increased when Drug b is combined with Drug a. |
| 29 | The risk or severity of hyperkalemia can be increased when Drug a is combined with Drug b. |
| 30 | The risk or severity of hypertension can be increased when Drug b is combined with Drug a. |
| 31 | The risk or severity of hypotension can be increased when Drug a is combined with Drug b. |
| 32 | The risk or severity of QTc prolongation can be increased when Drug a is combined with Drug b. |
| 33 | Drug a may decrease the analgesic activities of Drug b. |
| 34 | Drug a may decrease the anticoagulant activities of Drug b. |
| 35 | Drug a may decrease the antihypertensive activities of Drug b. |
| 36 | Drug a may decrease the antiplatelet activities of Drug b. |
| 37 | Drug a may decrease the bronchodilatory activities of Drug b. |
| 38 | Drug a may decrease the diuretic activities of Drug b. |
| 39 | Drug a may decrease the neuromuscular blocking activities of Drug b. |
| 40 | Drug a may decrease the sedative activities of Drug b. |
| 41 | Drug a may decrease the stimulatory activities of Drug b. |

TABLE 11-continued

| Interaction No. | Sentence describing interaction |
|---|---|
| 42 | Drug a may decrease the vasoconstricting activities of Drug b. |
| 43 | Drug a may increase the adverse neuromuscular activities of Drug b. |
| 44 | Drug a may increase the analgesic activities of Drug b. |
| 45 | Drug a may increase the anticholinergic activities of Drug b. |
| 46 | Drug a may increase the anticoagulant activities of Drug b. |
| 47 | Drug a may increase the antihypertensive activities of Drug b. |
| 48 | Drug a may increase the antiplatelet activities of Drug b. |
| 49 | Drug a may increase the antipsychotic activities of Drug b. |
| 50 | Drug a may increase the arrhythmogenic activities of Drug b. |
| 51 | Drug a may increase the atrioventricular blocking (AV block) activities of Drug b. |
| 52 | Drug a may increase the bradycardic activities of Drug b. |
| 53 | Drug a may increase the bronchoconstrictory activities of Drug b. |
| 54 | Drug a may increase the central nervous system depressant (CNS depressant) activities of Drug b. |
| 55 | Drug a may increase the central nervous system depressant (CNS depressant) and hypertensive activities of Drug b. |
| 56 | Drug a may increase the constipating activities of Drug b. |
| 57 | Drug a may increase the dermatologic adverse activities of Drug b. |
| 58 | Drug a may increase the fluid retaining activities of Drug b. |
| 59 | Drug a may increase the hypercalcemic activities of Drug b. |
| 60 | Drug a may increase the hyperglycemic activities of Drug b. |
| 61 | Drug a may increase the hyperkalemic activities of Drug b. |
| 62 | Drug a may increase the hypertensive activities of Drug b. |
| 63 | Drug a may increase the hypocalcemic activities of Drug b. |
| 64 | Drug a may increase the hypoglycemic activities of Drug b. |
| 65 | Drug a may increase the hypokalemic activities of Drug b. |
| 66 | Drug a may increase the hyponatremic activities of Drug b. |
| 67 | Drug a may increase the hypotensive activities of Drug b. |
| 68 | Drug a may increase the hypotensive and central nervous system depressant (CNS depressant) activities of Drug b. |
| 69 | Drug a may increase the immunosuppressive activities of Drug b. |
| 70 | Drug a may increase the myelosuppressive activities of Drug b. |
| 71 | Drug a may increase the myopathic rhabdomyolysis activities of Drug b. |
| 72 | Drug a may increase the neuroexcitatory activities of Drug b. |
| 73 | Drug a may increase the neuromuscular blocking activities of Drug b. |
| 74 | Drug a may increase the orthostatic hypotensive activities of Drug b. |
| 75 | Drug a may increase the photosensitizing activities of Drug b. |
| 76 | Drug a may increase the QTc-prolonging activities of Drug b. |
| 77 | Drug a may increase the respiratory depressant activities of Drug b. |
| 78 | Drug a may increase the sedative activities of Drug b. |
| 79 | Drug a may increase the serotonergic activities of Drug b. |
| 80 | Drug a may increase the stimulatory activities of Drug b. |
| 81 | Drug a may increase the tachycardic activities of Drug b. |
| 82 | Drug a may increase the thrombogenic activities of Drug b. |
| 83 | Drug a may increase the ulcerogenic activities of Drug b. |
| 84 | Drug a may increase the vasoconstricting activities of Drug b. |
| 85 | Drug a may increase the vasodilatory activities of Drug b. |
| 86 | Drug a may increase the vasopressor activities of Drug b.; | and
predicting a mechanism of action of the interaction between the two compounds through the output sentence;
wherein the interaction is a mechanism of action or activity information.

2. The method according to claim 1, wherein the compound is a drug or food ingredient.

3. The method according to claim 1, wherein a case for which the interaction is not predicted is a combination of compounds having a low probability of adverse interaction.

4. A computer-implemented method for screening a drug combination having a low probability of adverse interaction using structural information of a drug, the method comprising:
calculating a structural similarity profile of each of two compounds of interest for prediction of an interaction therebetween through comparison of a structural similarity between the each compound and any of different predefined compounds by using the following Equation 1 or Equation 2:

$$\text{Tanimoto coefficient}(a, a') = \frac{|a \cap a'|}{|a \cup a'|} \quad [\text{Equation 1}]$$

$$\text{Cosine similarity}(a, a') = \frac{|a \cdot a|}{\|a\|\|a'\|}; \quad [\text{Equation 2}]$$

inputting the calculated structural similarity profile of the each of two compounds into a trained deep neural network model;
predicting an interaction between the two compounds by the deep neural network model using the input structural similarity profile; and
determining as a combination of compounds having a low probability of adverse interaction when the interaction is not predicted;
wherein a case for which the interaction is not predicted has an output value of the structural similarity profile of 0.47 or less and
wherein the interaction is a mechanism of action or activity information.

5. The method according to claim 4, wherein the compound is a drug or food ingredient.

* * * * *